US011832992B2

(12) United States Patent
Zhu et al.

(10) Patent No.: US 11,832,992 B2
(45) Date of Patent: Dec. 5, 2023

(54) SHEAR WAVE PROPAGATION SPEED DETERMINATION METHOD AND DEVICE

(71) Applicant: SONOSCAPE MEDICAL CORP., Guangdong (CN)

(72) Inventors: Chaochao Zhu, Guangdong (CN); Deqing Liu, Guangdong (CN); Naizhang Feng, Guangdong (CN)

(73) Assignee: SONOSCAPE MEDICAL CORP., Guangdong (CN)

( * ) Notice: Subject to any disclaimer, the term of this patent is extended or adjusted under 35 U.S.C. 154(b) by 618 days.

(21) Appl. No.: 17/052,191

(22) PCT Filed: Dec. 20, 2018

(86) PCT No.: PCT/CN2018/122214
§ 371 (c)(1),
(2) Date: Nov. 1, 2020

(87) PCT Pub. No.: WO2019/218669
PCT Pub. Date: Nov. 21, 2019

(65) Prior Publication Data
US 2021/0137499 A1    May 13, 2021

(30) Foreign Application Priority Data
May 17, 2018   (CN) .......................... 201810475875.5

(51) Int. Cl.
*A61B 8/12*    (2006.01)
*A61B 8/08*    (2006.01)
*G01N 29/04*   (2006.01)

(52) U.S. Cl.
CPC ........... *A61B 8/485* (2013.01); *G01N 29/041* (2013.01); *G01N 29/043* (2013.01)

(58) Field of Classification Search
CPC ................ G01N 29/041; G01N 29/043; G01S 7/52022; G01S 7/52042; A61B 8/469; A61B 8/485; A61B 8/5223
See application file for complete search history.

(56) References Cited

U.S. PATENT DOCUMENTS 8,753,277 B2   6/2014   McAleavey
2010/0016718 A1   1/2010   Fan et al.
(Continued)

FOREIGN PATENT DOCUMENTS

CN   103300890 A   9/2013
CN   103462643 A   12/2013
(Continued)

OTHER PUBLICATIONS

International Search Report for PCT/CN2018/122214 dated Feb. 27, 2019, ISA/CN.

*Primary Examiner* — Mark D Remaly
(74) *Attorney, Agent, or Firm* — Yue (Robert) Xu; Apex Attorneys at Law, LLP

(57) ABSTRACT

A shear wave propagation speed determination method and device. The method comprises: when a shear wave propagates along a tissue region of interest, acquiring motion data of each preset position point in the tissue region of interest (step 301); determining a value of the motion data of each preset position point (step 302), wherein the magnitude of the value represents regularity of a propagation waveform of the shear wave; and if the value meets a first preset condition, determining, on the basis of the motion data of each preset position point in the tissue region of interest, a propagation speed of the shear wave at each preset position point in the tissue region of interest (step 303). The invention improves accuracy in determination of the propagation speed of a shear wave.

15 Claims, 4 Drawing Sheets

(56) References Cited

U.S. PATENT DOCUMENTS

| | | | |
|---|---|---|---|
| 2013/0245442 A1 | 9/2013 | Hazard et al. | |
| 2013/0267847 A1 | 10/2013 | Tamura | |
| 2017/0196533 A1 | 7/2017 | Labyed et al. | |
| 2017/0347990 A1 | 12/2017 | Watanabe | |

FOREIGN PATENT DOCUMENTS

| | | |
|---|---|---|
| CN | 104244838 A | 12/2014 |
| CN | 104546014 A | 4/2015 |
| CN | 107616814 A | 1/2018 |
| CN | 108852416 A | 11/2018 |
| JP | 2018038522 A | 3/2018 |
| WO | 2016209922 A1 | 12/2016 |
| WO | 2018046611 A1 | 3/2018 |

SHEAR WAVE PROPAGATION SPEED DETERMINATION METHOD AND DEVICE

This application is the national phase of International Application No. PCT/CN2018/122214, titled "SHEAR WAVE PROPAGATION SPEED DETERMINATION METHOD AND DEVICE", filed on Dec. 20, 2018, which claims the priority to Chinese Patent Application No. 201810475875.5, titled "METHOD AND APPARATUS FOR DETERMINING PROPAGATION SPEED OF SHEAR WAVE", filed on May 17, 2018 with the China National Intellectual Property Administration, which is incorporated herein by reference in its entirety.

FIELD

The present disclosure relates to the field of medical image processing, and in particular to a method and an apparatus for determining a propagation speed of a shear wave.

BACKGROUND

Shear wave elastography based on acoustic radiation force is an ultrasonic elastography technology for evaluating elasticity of tissue. A propagation speed of a shear wave is closely related to elasticity of human tissue. Therefore, the shear wave elastography is widely applied in analyzing and diagnosing a lesion in the human tissue. Specifically, the elasticity of the tissue may be determined based on the propagation speed of the shear wave in the tissue, to analyze whether there is a lesion in the tissue.

At present, it is necessary to first excite a preset pulse-emitting region based on a preset excitation parameter to generate a shear wave, and then determine a propagation speed of the shear wave in a tissue region of interest in biological tissue, so as to measure the elasticity of the tissue. For example, motion data when the shear wave passes preset positions in the tissue region of interest is determined at the preset positions sequentially. Propagation speeds of the shear wave when passing the preset positions are sequentially determined based on the motion data at the preset positions.

Accuracy in diagnosing whether there is a legion in the tissue is directly affected by accuracy in determining the propagation speed of the shear wave at each preset position in the tissue region of interest. At present, the accuracy is low in determining the propagation speed of the shear wave at each preset position in the tissue region of interest.

SUMMARY

In view of the above, a method for determining a propagation speed of a shear wave is provided according to embodiments of the present disclosure, so as to reduce an influence of an attenuated signal-to-noise ratio of the shear wave on accuracy in determining a propagation speed at each preset position. Thereby, accuracy is improved in determining the propagation speed of the shear wave passing each preset position in a tissue region of interest.

An apparatus for determining a propagation speed of a shear wave is further provided according to embodiments the present disclosure, so as to implement and apply the above method in practice.

Technical solutions according to embodiments of the present disclosure are as follows.

A method for determining a propagation speed of a shear wave is provided, including:
  acquiring motion data of each preset position in a tissue region of interest, during the shear wave propagating in the tissue region of interest;
  determining a value from the motion data of all preset positions, where magnitude of the value characterizes regularity of a propagation waveform of the shear wave; and
  determining a propagation speed of the shear wave at each preset position in the tissue region of interest, based on the current motion data of each preset position in the tissue region of interest, in response to the value meeting a first preset condition.

In one embodiment, after determining the value from the motion data of all preset positions, the method further includes:
  in response to the value not meeting the first preset condition,
  adjusting an excitation parameter for exciting the shear wave, and exciting to generate the shear wave propagating into the tissue region of interest based on the adjusted excitation parameter, until the value from the motion data of all preset positions in the tissue region of interest meets the first preset condition.

In one embodiment, a target pulse-emitting region for receiving an excitation pulse to generate the shear wave is determined from a biological tissue by:
  detecting whether tissue in a preset pulse-emitting region is in a solid state;
  determining the target pulse-emitting region from tissue in a depth same as that of the preset pulse-emitting region, in a case that the tissue in the preset pulse-emitting region is not in the solid state, where tissue in the target pulse-emitting region is in the solid state; and
  determining the preset pulse-emitting region to be the target pulse-emitting region, in a case that the tissue in the preset pulse-emitting region is in the solid state.

In one embodiment, detecting whether tissue in the preset pulse-emitting region is in the solid state includes:
  emitting an excitation pulse to the preset pulse-emitting region, based on a preset excitation parameter, to generate the shear wave propagating into the tissue region of interest;
  acquiring a B-mode ultrasonic image that includes a marked tissue region, in response to detecting an instruction for performing shear wave elastography, where the marked tissue region is generated by marking the preset pulse-emitting region;
  detecting whether tissue in the marked tissue region in the B-mode ultrasonic image is non-hypoechoic tissue;
  determining that the tissue in the preset pulse-emitting region is in the solid state, in a case that the tissue in the marked tissue region is the non-hypoechoic tissue; and
  determining that the tissue in the preset pulse-emitting region is not in the solid state, in a case that the tissue in the marked tissue region is hypoechoic tissue.

In one embodiment, after determining the propagation speed of the shear wave at each preset position in the tissue region of interest, the method further includes:
  acquiring a measurement tissue region preset in the tissue region of interest, where the measurement tissue region is for determining to-be-measured elasticity;
  acquiring a value of reliability for the propagation speed of the shear wave at each preset position;

determining a preset position at which the value of reliability meets a second preset condition, from the preset positions within the measurement tissue region; and determining a parameter for evaluating the to-be-measured elasticity of the tissue region of interest, based on the propagation speed of the shear wave at the preset position at which the value of reliability meets the second preset condition.

In an embodiment, after determining the parameter for evaluating the to-be-measured elasticity of the tissue region of interest, the method further includes:

displaying the propagation speed of the shear wave at each preset position in the tissue region of interest, and the parameter.

An apparatus for determining a propagation speed of a shear wave is further provided, including:

a first acquiring unit, configured to acquire motion data of each preset position in a tissue region of interest, during the shear wave propagating in the tissue region of interest;

a first determining unit, configured to determine a value from the motion data of all preset positions, where magnitude of the value characterizes regularity of a propagation waveform of the shear wave; and a second determining unit, configured to determine a propagation speed of the shear wave at each preset position in the tissue region of interest, based on the motion data of each preset position in the tissue region of interest, in response to the value determined by the first determining unit meeting a first preset condition.

In one embodiment, the apparatus further includes an exciting unit, configured to:

in response to the value determined by the first determining unit not meeting the first preset condition, adjust an excitation parameter for exciting the shear wave, and excite the shear wave propagating into the tissue region of interest based on the adjusted excitation parameter, until the value from the motion data of all preset positions in the tissue region of interest meets the first preset condition.

In one embodiment, the apparatus further includes a third determining unit, configured to determine a target pulse-emitting region for receiving an excitation pulse to generate the shear wave;

where the third determining unit includes:

a detecting subunit, configured to detect whether tissue in a preset pulse-emitting region is in a solid state;

a first determining subunit, configured to determine the target pulse-emitting region from tissue in a depth same as that of the preset pulse-emitting region, in a case that the detecting subunit detects that the tissue in the preset pulse-emitting region is not in the solid state, where tissue in the target pulse-emitting region is in the solid state; and a second determining subunit, configured to determine the preset pulse-emitting region to be the target pulse-emitting region, in a case that the detecting subunit detects that the tissue in the preset pulse-emitting region is in the solid state.

In one embodiment, the detecting subunit includes:

an exciting module, configured to emit an excitation pulse to the preset pulse-emitting region, based on a preset excitation parameter, to generate the shear wave propagating into the tissue region of interest;

an acquiring module, configured to acquire a B-mode ultrasonic image that includes a marked tissue region, in response to detecting an instruction for performing shear wave elastography, where the marked tissue region is generated by marking the preset pulse-emitting region;

a detecting module, configured to detect whether tissue in the marked tissue region in the B-mode ultrasonic image is non-hypoechoic tissue; and a determining module, configured to determine that the tissue in the preset pulse-emitting region is in the solid state in a case that the detecting module detects that the tissue in the marked tissue region is the non-hypoechoic tissue, and determine that the tissue in the preset pulse-emitting region is not in the solid state in a case that the detecting module detects that the tissue in the marked tissue region is hypoechoic tissue.

In one embodiment, the apparatus further includes:

a second acquiring unit, configured to acquire a measurement tissue region preset in the tissue region of interest, after the second determining unit determines the propagation speed of the shear wave at each preset position in the tissue region of interest, where the measurement tissue region is for determining to-be-measured elasticity;

a fourth determining unit, configured to determine a value of reliability for the propagation speed of the shear wave at each preset position in the measurement tissue region, based on the propagation speed of the shear wave at each preset position in the measurement tissue region;

a fifth determining unit, configured to determine a preset position at which the value of reliability meets a second preset condition, from the preset positions in the measurement tissue region; and a sixth determining unit, configured to determine a parameter for evaluating the to-be-measured elasticity of the tissue region of interest, based on the propagation speed of the shear wave at the preset position at which the value of reliability meets the second preset condition.

In one embodiment, the apparatus further includes:

a displaying unit, configured to display the propagation speed of the shear wave at each preset position in the tissue region of interest, and the parameter, after the sixth determining unit determines the parameter for evaluating the to-be-measured elasticity of the tissue region of interest.

The present disclosure has the following beneficial effects.

A signal-to-noise ratio of the shear wave propagating in the tissue region of interest is continuously attenuated by the tissue region of interest, and thereby a waveform of the shear wave is irregular during propagation. When a propagation speed of a shear wave passing a preset position in the tissue region of interest is determined with an irregular waveform, the determined propagation speed is greatly different from that corresponding to real elasticity of the tissue region of interest. That is, the determined propagation speed of the shear wave is inaccurate in comparison with that corresponding to the real elasticity. The value based on the motion data of all preset positions in the tissue region of interest is capable to reflect a degree of irregularity in the waveform of the shear wave during propagation. In an embodiment of the present disclosure, the propagation waveform of the shear wave is kept as regular as possible in the tissue region of interest after the signal-to-noise ratio is attenuated, when the value meets the first preset condition. In such case, the propagation speed of the shear wave determined based on the motion data of the preset positions in the tissue region of interest is close to that corresponding to the real elasticity. Thereby, accuracy of the determined propagation speed of the shear wave is improved.

BRIEF DESCRIPTION OF THE DRAWINGS

For clearer illustration of the technical solutions according to embodiments of the present disclosure or conventional techniques, hereinafter are briefly described the drawings to be applied in embodiments of the present disclosure or conventional techniques. Apparently, the drawings in the following descriptions are only some embodiments of the present disclosure, and other drawings may be obtained by those skilled in the art based on the provided drawings without creative efforts.

DETAILED DESCRIPTION OF EMBODIMENTS

Figure 1:
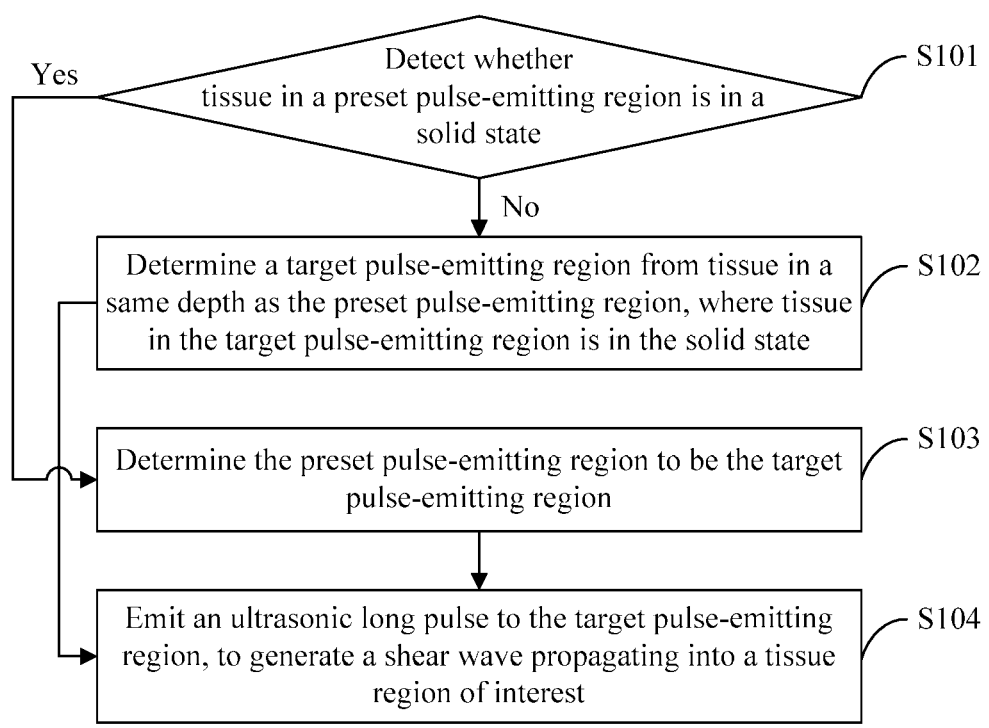
FIG. 1 is a flowchart of a method for exciting a shear wave according to an embodiment of the present disclosure.

Hereinafter technical solutions in embodiments of the present disclosure are described clearly and completely in conjunction with the drawings in embodiments of the present closure. Apparently, the described embodiments are only some rather than all of the embodiments of the present disclosure. Any other embodiments obtained based on the embodiments of the present disclosure by those skilled in the art without any creative effort fall within the scope of protection of the present disclosure.

In practice, a tissue region in which tissue elasticity is to be determined is selected by a user. The tissue region selected by the user is referred to as a tissue region of interest in embodiments of the present disclosure, to facilitate description. Tissue elasticity in the tissue region of interest may be determined based on a propagation speed of a shear wave in the tissue region of interest. Before determining the propagation speed of the shear wave in the tissue region of interest, the user enters a module for shear wave elastography, and selects the tissue region of interest. A system emits an ultrasonic pulse, for example, an ultrasonic long pulse, to a preset pulse-emitting region in the tissue region of interest, so as to generate a shear wave that propagates into the tissue region of interest. The preset pulse-emitting region may be located at a left or right side of the tissue region of interest, or within the tissue region of interest.

After the tissue region of interest and the preset pulse-emitting region are determined, a process of exciting the preset pulse-emitting region to generate the shear wave may be as follows. A focused ultrasonic long pulse with high energy is emitted, by an ultrasonic probe, into a preset pulse-emitting region at a preset depth. The emitted focused ultrasonic long pulses may last for hundreds to thousands of periods, that is, last for tens to hundreds of microseconds. Thereby, acoustic radiation force is generated. The generated acoustic radiation force interacts with tissue in the preset pulse-emitting region, and a large portion of the acoustic radiation force is absorbed by the tissue in the preset pulse-emitting region. Consequently, the tissue in the preset pulse-emitting region vibrates to generate shear deformation, and thereby a shear wave is generated in the tissue of the preset pulse-emitting region. The generated shear wave propagates left and right, so that the shear wave passes through the tissue region of interest.

After the tissue in the preset pulse-emitting region is excited to generate the shear wave, a propagation speed of the shear wave that propagates in the tissue region of interest is determined. The shear wave generated by exciting the tissue in the preset pulse-emitting region cannot propagate, in a case that the tissue in the preset pulse-emitting region into which the focused ultrasonic long pulse is emitted is in a non-solid state, such as gas or liquid. Therefore, accuracy is low in subsequent determination of the propagation speed in the tissue region of interest, for the shear wave that is generated in the preset pulse-emitting region. In view of the above, a method for exciting a shear wave is provided according to an embodiment of the present disclosure. In this method embodiment, it is determined whether the tissue in the preset pulse-emitting region is in a solid state, by utilizing a characteristic that tissue of the non-solid state is hypoechoic. In a case that the tissue in the preset pulse-emitting region is in the non-solid state, it is necessary to find a target pulse-emitting region in which tissue is in the solid state. Accordingly, the ultrasonic pulse is emitted to the target pulse-emitting region, to generate the shear wave that propagates into the tissue region of interest.

Reference is made to FIG. 1, which is a flowchart of a method for exciting a shear wave according to an embodiment of the present disclosure. This method embodiment may include steps 101 to 104.

In step 101, it is detected whether tissue in a preset pulse-emitting region is in a solid state.

In this step, the preset pulse-emitting region is a pulse-emitting region designated by a user. At beginning, it is unknown to the user whether the tissue in the designated pulse-emitting region is in the solid state. Therefore, in this step, it is detected whether the tissue in the preset pulse-emitting region is in the solid state.

In this embodiment, it may be detected whether the tissue in the preset pulse-emitting region is in the solid state through following steps A1 to A3.

In step A1, an excitation pulse is emitted to the preset pulse-emitting region, based on a preset excitation parameter, to generate a shear wave propagating into the tissue region of interest.

In this step, the preset excitation parameter may be predetermined by the user in advance. The excitation pulse, such as an ultrasonic long pulse, is emitted to the preset pulse-emitting region by a system, based on the preset excitation parameter, so as to generate the shear wave that propagates into the tissue region of interest. The excitation parameter includes: duration of each emitted ultrasonic long pulse, an excitation position, an excitation depth, and the like.

In step A2, a B-mode ultrasonic image including a marked tissue region is acquired, in response to detecting an instruction for performing shear wave elastography.

The excitation pulse is emitted to the preset pulse-emitting region, generating the shear wave that propagates into the tissue region of interest. After the shear wave that propagates into the tissue region of interest is generated, the user selects a process for entering shear wave elastography.

For example, the user presses a button that represents the shear wave elastography, and the instruction for performing the shear wave elastography is transmitted. When entering the shear wave elastography, a marked area including the preset pulse-emitting region is marked by the user and displayed in a device for shear wave elastography. Such marked area is referred to as the marked tissue region, to facilitate description.

In this step, the B-mode ultrasonic image including the marked tissue region is acquired, in response to detecting the instruction for performing shear wave elastography.

In step A3, it is detected whether tissue in the marked tissue region in the B-mode ultrasonic image is non-hypoechoic tissue.

It is detected whether the tissue in the marked area in the B-mode ultrasonic image is the non-hypoechoic tissue in this step, after the marked area in the B-mode ultrasonic image is acquired. In a case that the tissue in the marked tissue region is the non-hypoechoic tissue, the tissue in the preset pulse-emitting region is in the solid state. In a case that the tissue in the marked tissue region is hypoechoic tissue, the tissue in the preset pulse-emitting region is not in the solid state.

In step 102, a target pulse-emitting region is determined from tissue in a depth same as that of the preset pulse-emitting region, in a case that the tissue in the preset pulse-emitting region is not in the solid state, where tissue in the target pulse-emitting region is in the solid state.

This step is performed when it is detected that the tissue in the preset pulse-emitting region is not in the solid state. In a specific embodiment, a pulse-emitting region in which tissue is in the solid state is determined from the tissue in the same depth as the preset pulse-emitting region. In this embodiment, the pulse-emitting region in which the tissue is in the solid state is referred to as the target pulse-emitting region, to facilitate description.

In a specific embodiment, a process of determining the target pulse-emitting region may be as follows. A target region not intersecting with the preset pulse-emitting region is determined from the tissue in the same depth as the preset pulse-emitting region. Then, it is detected whether the target region is in the solid state. A next target region is determined in a case that the target region is not in solid state, until a determined target area is in the solid state. The determined target area in which the tissue is in the solid state is determined to be the target pulse-emitting region.

In step 103, the preset pulse-emitting region is determined to be the target pulse-emitting region, in a case that the tissue in the preset pulse-emitting region is in the solid state.

This step is performed in a case that the tissue in the preset pulse-emitting region is in the solid state. The preset pulse-emitting region is directly determined as the target pulse-emitting region.

In step 104, an ultrasonic long pulse is emitted to the target pulse-emitting region, so as to generate the shear wave propagating into the tissue region of interest.

The excitation pulse such as the ultrasonic long pulse is emitted to the target pulse-emitting region in this step, after the target pulse-emitting region is determined. Thereby, the shear wave that propagates to the tissue region of interest is generated.

The target pulse-emitting region determined in this embodiment is in the solid state. In such case, the shear wave generated by emitting the excitation pulse to the target pulse-emitting region is capable to propagate normally in the target pulse-emitting region. Avoided is an influence of the non-solid state of the preset pulse-emitting region on propagation of the shear wave. Therefore, avoided is a problem of low accuracy in subsequent determination of the propagation speed of the shear wave due to the non-solid state of the preset pulse-emitting region.

Energy for exciting the acoustic radiation force may be insufficient due to low excitation voltage, short duration of the excitation pulse, or a low repetition frequency of the pulses in sampling a motion signal of the shear wave, when considering a depth of tissue imaging, thicknesses of skin and subcutaneous fat tissue, and a degree of softness of an object in the tissue region of interest. In such case, a signal-to-noise ratio of the generated shear wave signal is low, and the generated shear wave is only capable to propagate within a certain distance. Further, propagation of the shear wave is in an irregular state, which directly results in low accuracy in the propagation speed of the shear wave that is generated in this process.

Figure 2:
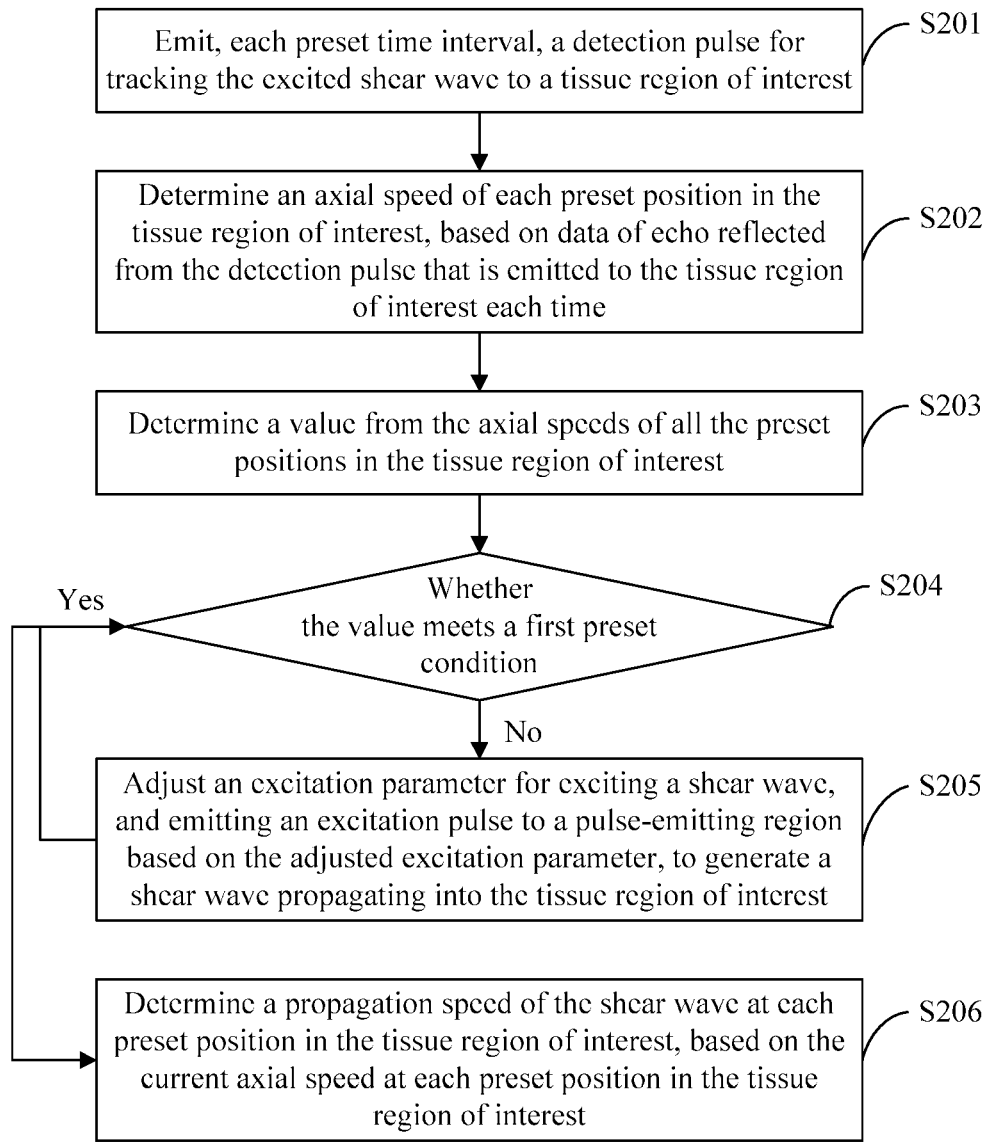
FIG. 2 is a flowchart of a method for determining a propagation speed of a shear wave according to an embodiment of the present disclosure.

When the signal-to-noise ratio of the generated shear wave signal is low, motion data of tissue positions in the tissue region of interest, and a value from the motion data of tissue positions in the tissue region of interest may be determined. Magnitude of such value reflects similarity between a waveform of the shear wave and a preset regular waveform. On such basis, a method for determining a propagation speed of a shear wave is provided according to an embodiment of the present disclosure, as shown in FIG. 2. In this method embodiment, it is determined whether the signal-to-noise ratio of the shear wave signal generated in the method embodiment as shown in FIG. 1 meets a requirement, by detecting whether the value from the motion data of preset positions in the tissue region of interest meets a first preset condition. This embodiment is a preferable embodiment that is performed after a shear wave is generated according to the method embodiment as shown in FIG. 1.

Reference is made to FIG. 2, which is a flowchart of a method for determining a propagation speed of a shear wave according to an embodiment of the present disclosure. This method embodiment may include steps 201 to 206.

In step 201, a detection pulse for tracking an excited shear wave is emitted, each preset time interval, to a tissue region of interest.

The detection pulse covering the tissue region of interest is emitted to the tissue region of interest each preset time interval. The detection pulse may be a non-focused single-angle planar ultrasonic beam, a non-focused multi-angle planar ultrasonic beam, a focused ultrasonic beam, or a wide ultrasonic beam. A form of the detection pulse is not specifically limited here.

In step 202, motion data of preset positions in the tissue region of interest is determined based on data of echo reflected from the detection pulse that is emitted each time to the tissue region of interest.

The data of the echo is collected after the detection pulse for tracking the shear wave propagating in the tissue region of interest is emitted to the tissue region of interest each preset time interval. The data of the echo is reflected from the detection pulse that is emitted to the tissue region of interest each time. Multi-beam synthesis is performed on the echo data collected each time, to obtain target data after multi-beam synthesis. The target data after multi-beam synthesis corresponds to the echo data collected each time. A certain algorithm is applied to the target tissue region, so as to determine the motion data of the preset positions in the tissue of the tissue region of interest.

The target data after multi-beam synthesis corresponding to the echo data collected each time may be RF data or IQ data. In a case that the target data is the RF data, the motion data is obtained based on the RF data through a cross-correlation algorithm. In a case that the target data is the IQ data, the motion data is obtained based on the IQ data through a tissue motion estimation algorithm, which is generally a Kasai algorithm and a Loupas algorithm.

The IQ data is acquired through hardware beam synthesis in most conventional ultrasound diagnostic apparatuses. The IQ data is obviously advantageous in comparison the RF data in following aspects. Not only an amount of data is greatly reduced without losing original information, but also phase information is included. A phase-shift estimation algorithm mainly includes a 1D autocorrelation algorithm of the Kasai algorithm and a 2D autocorrelation algorithm of the Loupas algorithm.

In step 203, a value from the motion data of all the preset positions in the tissue region of interest is determined.

In this embodiment, magnitude of the value from the motion data of the preset positions characterizes regularity of a propagation waveform of the shear wave. The value may be a mean for axial displacements, a variance for axial displacements, a mean for axial speeds, a variance for axial speeds, or a moment at which the shear wave reaches maximum. In practice, the value may be other parameters, and a specific type of the parameter characterizing the value is not limited here.

The value from the motion data of the preset positions is determined in this step, after the motion data of the preset positions in the tissue region of interest is determined.

In step 204, it is detected whether the value meets a first preset condition. The method goes to step 205, in a case that the value does not meet the first preset condition. The method goes to step S206, in a case that the value meets the first preset condition.

It is detected whether the value meets the first preset condition in this step, after the value from the motion data of all the preset positions in the tissue region of interest is determined. In a specific embodiment, the first preset condition may be being greater than a preset threshold, or may be being less than a preset threshold. In practice, sometimes the first preset condition is required to be being greater than the preset threshold, based on an actual situation. In such case, the value meets the first preset condition in a case that the value is greater than the preset threshold. Sometimes the first preset condition is required to be being less than the preset threshold. In such case, the value meets the first preset condition in a case that the value is less than the preset threshold. The first preset condition may be in other specific forms in a practical application scenario. A specific form of the first preset condition is not limited herein. The value meeting the first preset condition indicates a large similarity between a propagation waveform of a shear wave currently generated in the tissue region of interest and a preset regular waveform. Therefore, the propagation speed of the shear wave determined at each preset position is highly accurate.

The method goes to step 205, in a case that the value in current detection of this step does not meet the first preset condition. The method goes to step S206, in a case that the value in current detection meets the first preset condition.

In step 205, an excitation parameter for exciting the shear wave is adjusted, and an excitation pulse is emitted to the pulse-emitting region based on the adjusted excitation parameter, to generate the shear wave that propagates into the tissue region of interest. The method returns to step 204.

It indicates that a propagation state of the shear wave currently generated in the tissue region of interest is disordered, when the currently determined value does not meet the first preset condition. A reason for the disordered propagation state may be an inappropriate excitation parameter for exciting the shear wave. The excitation parameter may include: duration of emitting the ultrasonic pulse to the pulse-emitting region, an excitation voltage, an excitation depth, or the like. In this step, a manner of adjusting the excitation parameter may include increasing the duration of emitting the excitation pulse. In practice, the excitation parameter may be adjusted based on an actual situation. A manner of adjusting the excitation parameter is not specifically limited here.

The excitation pulse is emitted to the pulse-emitting region based on the adjusted excitation parameter, to generate the shear wave that propagates into the tissue region of interest. The method further returns to step 204.

In a preferable embodiment, the pulse-emitting region in this step is the target pulse-emitting region in the method embodiment as shown in FIG. 1, so as to achieve a better effect.

In step 206, a propagation speed of the shear wave at each preset position in the tissue region of interest is determined based on the motion data of each preset position in the tissue region of interest.

This step is performed when the value from the motion data of the preset positions in the tissue region of interest meets the first preset condition. In a specific embodiment, the propagation speed of the shear wave at each preset position in the tissue region of interest is determined in this step based on the motion data of each preset position in the tissue region of interest, that is, based on the motion data of each preset position in the tissue region of interest from which the value meets the first preset condition.

In these embodiments, a signal-to-noise ratio of the shear wave propagating in the tissue region of interest is continuously attenuated by the tissue region of interest, and thereby a waveform of the shear wave is irregular during propagation. When a propagation speed of a shear wave passing a preset position in the tissue region of interest is determined with an irregular waveform, the determined propagation speed is greatly different from that corresponding to real elasticity of the tissue region of interest. That is, the determined propagation speed of the shear wave is inaccurate in comparison with that corresponding to the real elasticity. The value based on the motion data of all preset positions in the tissue region of interest is capable to reflect a degree of irregularity in the waveform of the shear wave during propagation. In an embodiment of the present disclosure, the propagation waveform of the shear wave is kept as regular as possible in the tissue region of interest after the signal-to-noise ratio is attenuated, when the value meets the first preset condition. In such case, the propagation speed of the shear wave determined based on the motion data of the preset positions in the tissue region of interest is close to that corresponding to the real elasticity.

Thereby, accuracy of the determined propagation speed of the shear wave is improved.

Figure 3:
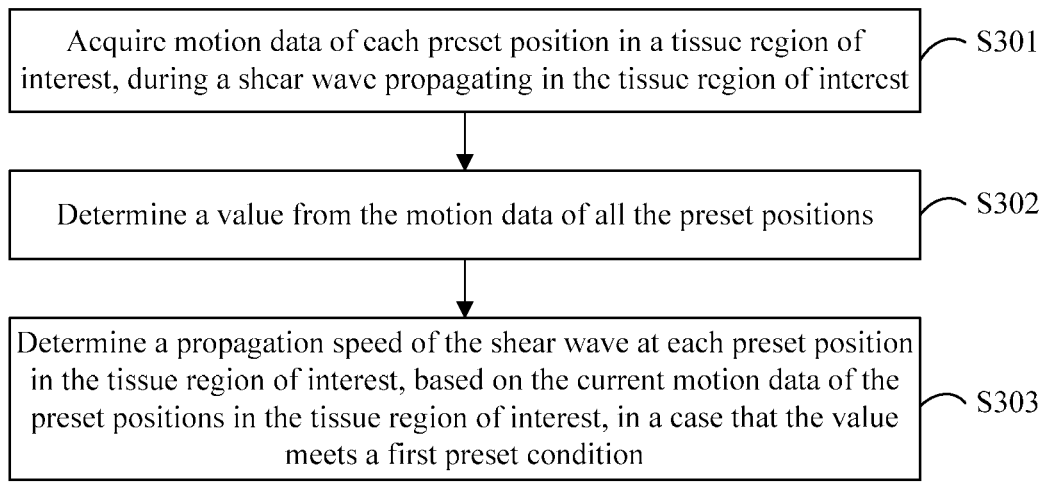
FIG. 3 is a flowchart of a method for determining a propagation speed of a shear wave according to another embodiment of the present disclosure.

Reference is made to FIG. 3, which is a flowchart of a method for determining a propagation speed of a shear wave according to another embodiment of the present disclosure. The method embodiment may include steps 301 to 303.

In step 301, motion data of each preset position in a tissue region of interest is acquired during the shear wave propagating in the tissue region of interest.

In this step, a process of acquiring the motion data of each preset position in the tissue region of interest may refer to the steps 201 to 202 in the method embodiment as shown in FIG. 2. Details are not repeated herein.

In step 302, a value is determined from the motion data of all the preset positions.

In this step, specific details may refer to the step 203 in the method embodiment as shown in FIG. 2. Details are not repeated herein.

In step 303, a propagation speed of the shear wave at each preset position in the tissue region of interest is determined based on the current motion data of each preset position in the tissue region of interest, in a case that the value meets a first preset condition.

In this step, specific details may refer to step 206 in the method embodiment as shown in FIG. 2. Details are not repeated herein.

In this embodiment, a method for determining a propagation speed of a shear wave is provided. A concept of determining a propagation speed of a shear wave is provided in this method embodiment. In practice, any embodiment that conforms to the concept provided in this embodiment is capable to achieve an objective of determining the propagation speed of the shear wave.

There may be a preset position with low reliability for the propagation speed of the shear wave in a region under measurement. Therefore, elasticity of to-be-measured tissue may be determined with low accuracy, when the propagation speed of the shear wave at each preset positions in the region under measurement is considered in determining a parameter for evaluating the elasticity of the to-be-measured tissue. Therefore, a method for determining a parameter for evaluating elasticity of to-be-measured tissue is provided according to an embodiment of the present disclosure, as shown by the flowchart in FIG. 4. In this method embodiment, a target preset position at which reliability of a propagation speed of the shear wave meets a preset condition is selected from the preset positions in a region under measurement. The parameter for evaluating the elasticity of the to-be-measured tissue is determined based on the propagation speed of the shear wave at the target preset position.

Figure 4:
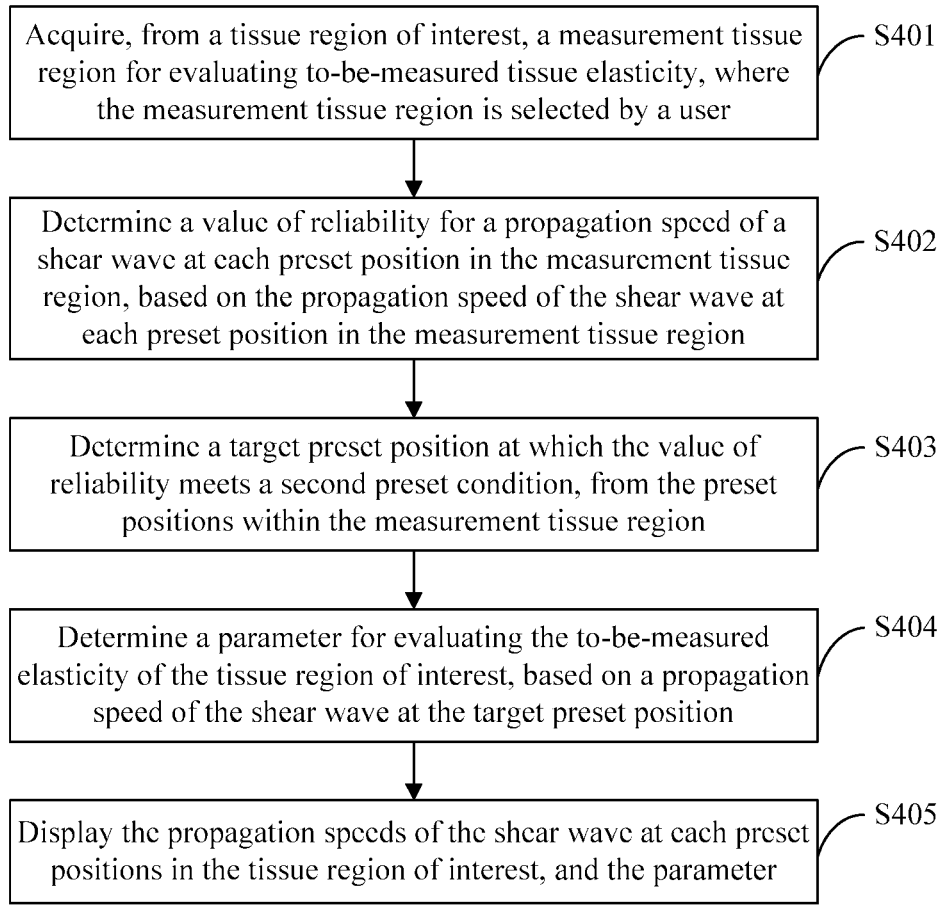
FIG. 4 is a flowchart of a method for determining a parameter for evaluating elasticity of to-be-measured tissue according to an embodiment of the present disclosure.

Reference is made to FIG. 4, which is a flowchart of a method for determining a parameter for evaluating elasticity of to-be-measured tissue. The method embodiment may include steps 401 to 405.

In step 401, a measurement tissue region for evaluating to-be-measured tissue elasticity is acquired from the tissue region of interest, where the measurement tissue region is selected by a user.

A preset region for evaluating the to-be-measured tissue elasticity is acquired from the tissue region of interest in this step, after the propagation speed of the shear wave at each preset position in the tissue region of interest is determined. The region for evaluating the to-be-measured tissue elasticity is referred to as the measurement tissue region, to facilitate description. The measurement tissue region is preset, for example, by the user. The measurement tissue region may be circular, rectangular, trapezoidal, or the like. The measurement tissue region may be in other shapes. A shape of the measurement tissue region is not specifically limited here.

In step 402, a value of reliability for a propagation speed of the shear wave at each preset position in the measurement tissue region is determined based on the propagation speed of the shear wave at each preset position in the measurement tissue region.

The value of reliability for the propagation speed of the shear wave at each preset position in the measurement tissue region is determined based on the propagation speed of the shear wave at each preset position in the measurement tissue region in this step, after the measurement tissue region preset in the tissue region of interest is acquired.

In step 403, a target preset position at which the value of reliability meets a second preset condition is determined from the preset positions in the measurement tissue region.

The preset position at which the value of value of reliability meets the second preset condition is selected from the measurement tissue region, after the value of reliability for the propagation speed of the shear wave at each preset position in the measurement tissue region is determined. In this embodiment, the selected preset position is referred to as the target preset position, to facilitate description. The second preset condition may be being greater than a preset reliability threshold, or may be being less than a preset reliability threshold. In practice, sometimes the second preset condition is required to be being greater than the preset reliability threshold, based on an actual situation. In such case, the value of reliability meets the second preset condition in a case that the value of reliability is greater than the preset reliability threshold. Sometimes the second preset condition is required to be being less than the preset reliability threshold. In such case, the value of reliability meets the second preset condition in a case that the value of reliability is less than the preset reliability threshold. The second preset condition may be in other specific forms in a practical application scenario. A specific form of the second preset condition is not limited herein.

In step 404, a parameter for evaluating the to-be-measured elasticity of the tissue region of interest is determined, based on the propagation speed of the shear wave at the target preset position.

The parameter for evaluating the to-be-measured elasticity of the tissue region of interest is determined based on the propagation speed of the shear wave at the target preset position in this step, after the target preset position is selected.

In step 405, the propagation speed of the shear wave at each preset position in the tissue region of interest, and the parameter, are displayed.

A matrix of the propagation speeds of the shear wave in the tissue region of interest is acquired, after the propagation speed of the shear wave at each preset position in the tissue region of interest is acquired. Through linear mapping, a floating-point matrix of the propagation speeds of the shear wave may be converted into a matrix of 0-255, that is, a matrix of 8-bit integers for the propagation speeds of the shear wave. The integer matrix of the propagation speeds of the shear wave may be displayed through gray-scale mapping, a pseudo-color algorithm, or a color algorithm. In addition, the determined parameter for evaluating the elasticity of the tissue region of interest may also be displayed.

In this embodiment, the target preset position at which reliability of the propagation speed of the shear wave meets the preset condition is determined based on reliability of the propagation speed of the shear wave at each preset position in the preset measurement tissue region, when determining tissue elasticity in the tissue region of interest. The reliability of the propagation speed of the shear wave at the target preset position is high. Therefore, accuracy of the parameter for evaluating the elasticity of the tissue region of interest can be improved due to being determined based on the propagation speed of the shear wave at the target preset position.

Figure 5:
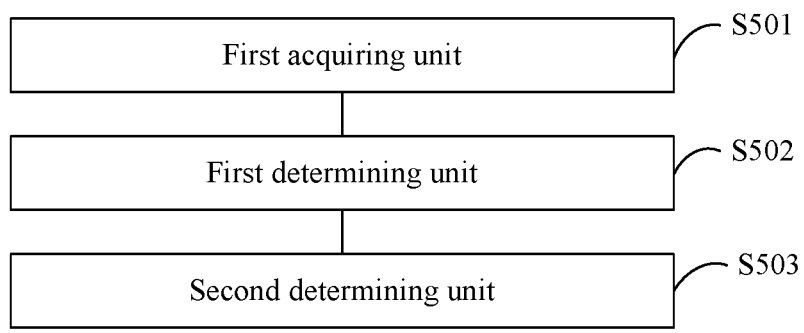
FIG. 5 is a schematic structural diagram of an apparatus for determining a propagation speed of a shear wave according to an embodiment of the present disclosure.

Reference is made to FIG. 5, which is a schematic structural diagram of an apparatus for determining a propagation speed of a shear wave according to an embodiment of the present disclosure. The apparatus may include a first acquiring unit 501, a first determining unit 502, and a second determining unit 503.

The first acquiring unit 501 is configured to acquire motion data of each preset position in a tissue region of interest, during the shear wave propagating in the tissue region of interest.

The first determining unit 502 is configured to determine a value from the motion data of all preset positions, where magnitude of the value characterizes regularity of a propagation waveform of the shear wave.

The second determining unit 503 is configured to determine a propagation speed of the shear wave at each preset position in the tissue region of interest, based on the motion data of each preset position in the tissue region of interest, in a case that the value determined by the first determining unit meets a first preset condition.

The apparatus may further include an exciting unit. The exciting unit is configured to, in a case that value determined by the first determining unit does not meet the first preset condition, adjust an excitation parameter for exciting the shear wave, and excite the shear wave propagating into the tissue region of interest based on the adjusted excitation parameter, until the value from the motion data of all preset positions in the tissue region of interest meets the first preset condition.

The apparatus may further include a third determining unit. The third determining unit is configured to determine a target pulse-emitting region for receiving an excitation pulse to generate the shear wave.

The third determining unit includes a detecting subunit, a first determining subunit, and a second determining subunit.

The detecting subunit is configured to detect whether tissue in a preset pulse-emitting region is in a solid state.

The first determining subunit is configured to determine the target pulse-emitting region from tissue in a depth same as that of the preset pulse-emitting region, in a case that the detecting subunit detects that the tissue in the preset pulse-emitting region is not in the solid state, where tissue in the target pulse-emitting region is in the solid state.

The second determining subunit is configured to determine the preset pulse-emitting region to be the target pulse-emitting region, in a case that the detecting subunit detects that the tissue in the preset pulse-emitting region is in the solid state.

The detecting subunit may include an exciting module, an acquiring module, a detecting module, and a determining module.

The exciting module is configured to emit an excitation pulse to the preset pulse-emitting region, based on a preset excitation parameter, to generate the shear wave propagating into the tissue region of interest.

The acquiring module is configured to acquire a B-mode ultrasonic image that includes a marked tissue region, in response to detecting an instruction for performing shear wave elastography, where the marked tissue region is generated by marking the preset pulse-emitting region.

The detecting module is configured to detect whether tissue in the marked tissue region in the B-mode ultrasonic image is non-hypoechoic tissue.

The determining module is configured to determine that the tissue in the preset pulse-emitting region is in the solid state in a case that the detecting module detects that the tissue in the marked tissue region is the non-hypoechoic tissue, and determine that the tissue in the preset pulse-emitting region is not in the solid state in a case that the detecting module detects that the tissue in the marked tissue region is hypoechoic tissue.

The apparatus may further include a second acquiring unit, a fourth determining unit, a fifth determining unit, and a sixth determining unit.

The second acquiring unit is configured to acquire a measurement tissue region preset in the tissue region of interest, after the second determining unit determines the propagation speed of the shear wave at each preset position in the tissue region of interest, where the measurement tissue region is for determining to-be-measured elasticity.

The fourth determining unit is configured to determine a value of reliability for the propagation speed of the shear wave at each preset position in the measurement tissue region, based on the propagation speed of the shear wave at each preset position in the measurement tissue region.

The fifth determining unit is configured to determine a target preset position at which the value of reliability meets a second preset condition, from the preset positions in the measurement tissue region.

The sixth determining unit is configured to determine a parameter for evaluating the to-be-measured elasticity of the tissue region of interest, based on the propagation speed of the shear wave at the target preset position.

The apparatus may further include a displaying unit. The displaying unit is configured to display the propagation speed of the shear wave at each preset position in the tissue region of interest, and the parameter, after the sixth determining unit determines the parameter for evaluating the to-be-measured elasticity of the tissue region of interest.

In practice, implementation of the method embodiments for exciting the shear wave, for determining the propagation speed of the shear wave, and for determining the tissue elasticity of the tissue region of interest may be included in this apparatus embodiment, so as to ensure an effect achieved in the above method embodiments.

The embodiments of the present disclosure are described in a progressive manner, and each embodiment places emphasis on the difference from other embodiments. Therefore, one embodiment can refer to other embodiments for the same or similar parts. The relationship terms such as "first", "second" and the like herein are only used herein to distinguish one entity or operation from another, rather than to necessitate or imply that an actual relationship or order exists between the entities or operations. Furthermore, the terms such as "include", "comprise" or any other variants thereof means to be inclusive rather than exclusive, namely, means to be "including but not limited to". All variants, equivalent replacements, improvements and the like made without departing from the concept of the present disclosure fall within the protection scope of the present disclosure.

According to the description of the disclosed embodiments, those skilled in the art can implement or use the present disclosure. Various modifications made to these embodiments may be obvious to those skilled in the art, and the general principle defined herein may be implemented in other embodiments without departing from the spirit or scope of the present disclosure. Therefore, the present disclosure is not limited to the embodiments described herein but confirms to a widest scope in accordance with principles and novel features disclosed in the present disclosure.

The invention claimed is:

1. A method for determining a propagation speed of a shear wave, comprising:
   acquiring motion data of each preset position in a tissue region of interest, during the shear wave propagating in the tissue region of interest;
   determining a value from the motion data of all preset positions, wherein magnitude of the value characterizes regularity of a propagation waveform of the shear wave; and
   determining a propagation speed of the shear wave at each preset position in the tissue region of interest, based on the current motion data of each preset position in the tissue region of interest, in response to the value meeting a first preset condition.

2. The method according to claim 1, wherein after determining the value from the motion data of all preset positions, the method further comprises:
   in response to the value not meeting the first preset condition,
   adjusting an excitation parameter for exciting the shear wave, and exciting to generate the shear wave propagating into the tissue region of interest based on the adjusted excitation parameter, until the value from the motion data of all preset positions in the tissue region of interest meets the first preset condition.

3. The method according to claim 2, wherein after determining the propagation speed of the shear wave at each preset position in the tissue region of interest, the method further comprises:
   acquiring a measurement tissue region preset in the tissue region of interest, wherein the measurement tissue region is for determining to-be-measured elasticity;
   acquiring a value of reliability for the propagation speed of the shear wave at each preset position;
   determining a preset position at which the value of reliability meets a second preset condition, from the preset positions within the measurement tissue region; and
   determining a parameter for evaluating the to-be-measured elasticity of the tissue region of interest, based on the propagation speed of the shear wave at the preset position at which the value of reliability meets the second preset condition.

4. The method according to claim 1, wherein a target pulse-emitting region for receiving an excitation pulse to generate the shear wave is determined from a biological tissue by:
   detecting whether tissue in a preset pulse-emitting region is in a solid state;
   determining the target pulse-emitting region from tissue in a depth same as that of the preset pulse-emitting region, in a case that the tissue in the preset pulse-emitting region is not in the solid state, wherein tissue in the target pulse-emitting region is in the solid state; and
   determining the preset pulse-emitting region to be the target pulse-emitting region, in a case that the tissue in the preset pulse-emitting region is in the solid state.

5. The method according to claim 4, wherein after determining the propagation speed of the shear wave at each preset position in the tissue region of interest, the method further comprises:
   acquiring a measurement tissue region preset in the tissue region of interest, wherein the measurement tissue region is for determining to-be-measured elasticity;
   acquiring a value of reliability for the propagation speed of the shear wave at each preset position;
   determining a preset position at which the value of reliability meets a second preset condition, from the preset positions within the measurement tissue region; and
   determining a parameter for evaluating the to-be-measured elasticity of the tissue region of interest, based on the propagation speed of the shear wave at the preset position at which the value of reliability meets the second preset condition.

6. The method according to claim 4, wherein detecting whether tissue in the preset pulse-emitting region is in the solid state comprises:
   emitting an excitation pulse to the preset pulse-emitting region, based on a preset excitation parameter, to generate the shear wave propagating into the tissue region of interest;
   acquiring a B-mode ultrasonic image that comprises a marked tissue region, in response to detecting an instruction for performing shear wave elastography, wherein the marked tissue region is generated by marking the preset pulse-emitting region;
   detecting whether tissue in the marked tissue region in the B-mode ultrasonic image is non-hypoechoic tissue;
   determining that the tissue in the preset pulse-emitting region is in the solid state, in a case that the tissue in the marked tissue region is the non-hypoechoic tissue; and
   determining that the tissue in the preset pulse-emitting region is not in the solid state, in a case that the tissue in the marked tissue region is hypoechoic tissue.

7. The method according to claim 6, wherein after determining the propagation speed of the shear wave at each preset position in the tissue region of interest, the method further comprises:
   acquiring a measurement tissue region preset in the tissue region of interest, wherein the measurement tissue region is for determining to-be-measured elasticity;
   acquiring a value of reliability for the propagation speed of the shear wave at each preset position;
   determining a preset position at which the value of reliability meets a second preset condition, from the preset positions within the measurement tissue region; and
   determining a parameter for evaluating the to-be-measured elasticity of the tissue region of interest, based on the propagation speed of the shear wave at the preset position at which the value of reliability meets the second preset condition.

8. The method according to claim 1, wherein after determining the propagation speed of the shear wave at each preset position in the tissue region of interest, the method further comprises:
   acquiring a measurement tissue region preset in the tissue region of interest, wherein the measurement tissue region is for determining to-be-measured elasticity;
   acquiring a value of reliability for the propagation speed of the shear wave at each preset position;
   determining a preset position at which the value of reliability meets a second preset condition, from the preset positions within the measurement tissue region; and
   determining a parameter for evaluating the to-be-measured elasticity of the tissue region of interest, based on the propagation speed of the shear wave at the preset position at which the value of reliability meets the second preset condition.

9. The method according to claim 8, wherein after determining the parameter for evaluating the to-be-measured elasticity of the tissue region of interest, the method further comprises:
displaying the propagation speed of the shear wave at each preset position in the tissue region of interest, and the parameter.

10. An apparatus for determining a propagation speed of a shear wave, comprising:
a first acquiring unit, configured to acquire motion data of each preset position in a tissue region of interest, during the shear wave propagating in the tissue region of interest;
a first determining unit, configured to determine a value from the motion data of all preset positions, wherein magnitude of the value characterizes regularity of a propagation waveform of the shear wave; and
a second determining unit, configured to determine a propagation speed of the shear wave at each preset position in the tissue region of interest, based on the motion data of each preset position in the tissue region of interest, in response to the value determined by the first determining unit meeting a first preset condition.

11. The apparatus according to claim 10, further comprising:
an exciting unit, configured to:
in response to the value determined by the first determining unit not meeting the first preset condition,
adjust an excitation parameter for exciting the shear wave, and excite the shear wave propagating into the tissue region of interest based on the adjusted excitation parameter, until the value from the motion data of all preset positions in the tissue region of interest meets the first preset condition.

12. The apparatus according to claim 10, further comprising:
a third determining unit, configured to determine a target pulse-emitting region for receiving an excitation pulse to generate the shear wave, wherein:
the third determining unit comprises:
a detecting subunit, configured to detect whether tissue in a preset pulse-emitting region is in a solid state;
a first determining subunit, configured to determine the target pulse-emitting region from tissue in a depth same as that of the preset pulse-emitting region, in a case that the detecting subunit detects that the tissue in the preset pulse-emitting region is not in the solid state, wherein tissue in the target pulse-emitting region is in the solid state; and
a second determining subunit, configured to determine the preset pulse-emitting region to be the target pulse-emitting region, in a case that the detecting subunit detects that the tissue in the preset pulse-emitting region is in the solid state.

13. The apparatus according to claim 12, wherein the detecting subunit comprises:
an exciting module, configured to emit an excitation pulse to the preset pulse-emitting region, based on a preset excitation parameter, to generate the shear wave propagating into the tissue region of interest;
an acquiring module, configured to acquire a B-mode ultrasonic image that comprises a marked tissue region, in response to detecting an instruction for performing shear wave elastography, wherein the marked tissue region is generated by marking the preset pulse-emitting region;
a detecting module, configured to detect whether tissue in the marked tissue region in the B-mode ultrasonic image is non-hypoechoic tissue; and
a determining module, configured to determine that the tissue in the preset pulse-emitting region is in the solid state in a case that the detecting module detects that the tissue in the marked tissue region is the non-hypoechoic tissue, and determine that the tissue in the preset pulse-emitting region is not in the solid state in a case that the detecting module detects that the tissue in the marked tissue region is hypoechoic tissue.

14. The apparatus according to claim 10, further comprising:
a second acquiring unit, configured to acquire a measurement tissue region preset in the tissue region of interest, after the second determining unit determines the propagation speed of the shear wave at each preset position in the tissue region of interest, wherein the measurement tissue region is for determining to-be-measured elasticity;
a fourth determining unit, configured to determine a value of reliability for the propagation speed of the shear wave at each preset position in the measurement tissue region, based on the propagation speed of the shear wave at each preset position in the measurement tissue region;
a fifth determining unit, configured to determine a preset position at which the value of reliability meets a second preset condition, from the preset positions in the measurement tissue region; and
a sixth determining unit, configured to determine a parameter for evaluating the to-be-measured elasticity of the tissue region of interest, based on the propagation speed of the shear wave at the preset position at which the value of reliability meets the second preset condition.

15. The apparatus according to claim 14, further comprising:
a displaying unit, configured to display the propagation speed of the shear wave at each preset position in the tissue region of interest, and the parameter, after the sixth determining unit determines the parameter for evaluating the to-be-measured elasticity of the tissue region of interest.

* * * * *